US012806135B2

(12) United States Patent
Turzi et al.

(10) Patent No.: US 12,806,135 B2
(45) **Date of Patent: *Nov. 24, 2026**

(54) PREPARATION METHOD AND CONTAINER FOR A TOPICAL WOUND HEALING GEL

(71) Applicant: RegenLab USA LLC, Brooklyn, NY (US)

(72) Inventors: Antoine Turzi, Lauenen b. Gstaad (CH); Farid Gomri, Prilly (CH); Hosni Trabelsi, Brooklyn, NY (US)

(73) Assignee: RegenLabs USA LLC, Brooklyn, NY (US)

( * ) Notice: Subject to any disclaimer, the term of this patent is extended or adjusted under 35 U.S.C. 154(b) by 220 days.

This patent is subject to a terminal disclaimer.

(21) Appl. No.: 18/574,036

(22) PCT Filed: Jun. 24, 2022

(86) PCT No.: PCT/EP2022/067349

§ 371 (c)(1),
(2) Date: Dec. 24, 2023

(87) PCT Pub. No.: WO2022/269035

PCT Pub. Date: Dec. 29, 2022

(65) Prior Publication Data

US 2025/0275914 A1 Sep. 4, 2025

Related U.S. Application Data

(60) Provisional application No. 63/215,153, filed on Jun. 25, 2021.

(51) Int. Cl.

| | |
|---|---|
| ***A61K 9/00*** | (2006.01) |
| ***A61K 31/191*** | (2006.01) |
| ***A61K 31/194*** | (2006.01) |
| ***A61K 31/728*** | (2006.01) |
| ***A61K 35/16*** | (2015.01) |
| ***A61K 35/28*** | (2015.01) |

(52) U.S. Cl.

CPC .......... *A61K 9/0014* (2013.01); *A61K 31/191* (2013.01); *A61K 31/194* (2013.01); *A61K 31/728* (2013.01); *A61K 35/16* (2013.01); *A61K 35/28* (2013.01)

(58) Field of Classification Search

CPC ........... A61L 2300/42; A61L 2300/418; A61L 2202/23

See application file for complete search history.

(56) References Cited

U.S. PATENT DOCUMENTS

| | | | | |
|---|---|---|---|---|
| 4,021,340 | A * | 5/1977 | Zine, Jr. | G01N 33/491 252/60 |
| 8,945,537 | B2 * | 2/2015 | Turzi | A61L 26/0066 424/93.7 |
| 9,517,255 | B2 * | 12/2016 | Turzi | A61P 17/02 |
| 10,226,516 | B2 * | 3/2019 | Turzi | A61P 17/00 |
| 2013/0058906 | A1 | 3/2013 | Turzi | |
| 2017/0087228 | A1 * | 3/2017 | Turzi | C12Y 304/21005 |
| 2023/0133549 | A1 * | 5/2023 | Turzi | A61P 31/14 435/372 |

FOREIGN PATENT DOCUMENTS

| | | | | |
|---|---|---|---|---|
| EP | 3223875 A2 | 10/2017 | | |
| WO | WO-2008009642 A1 * | 1/2008 | | C12N 5/0037 |

OTHER PUBLICATIONS

Turzi, A., PCT/EP2022/067349, International Search Report, Oct. 17, 2022, 5 pages.

Turzi, A., PCT/EP2022/067349, Written Opinion, Oct. 17, 2022, 9 pages.

Murphy, M., et al., "Bone marrow concentrate and platelet-rich plasma acquisition and preparation: Why technique matters," Techniques in Regional Anesthesia and Pain Management, vol. 19, No. 1, Nov. 22, 2016, pp. 1-25.

* cited by examiner

*Primary Examiner* — Mark V Stevens
(74) *Attorney, Agent, or Firm* — Rahman LLC

(57) ABSTRACT

The present invention relates to a container for use in the preparation of a topical gel or topical membrane or topical patch formed from a PRP or BMC-coagulation activator combination, in which the container is prefilled with or comprises at least one thixotropic gel and a composition comprising at least one coagulation activator.

19 Claims, 8 Drawing Sheets

PREPARATION METHOD AND CONTAINER FOR A TOPICAL WOUND HEALING GEL

TECHNICAL FIELD

The containers, compositions, uses and methods described herein relate to isolated plasma-derived products or bone marrow-derived products for use as a drug/medicament, or for use in wound healing or for use as a topical gel, topical membrane or topical patch.

BACKGROUND

Conventional membranes and patches for use in wound healing or wound care are complicated to produce. The process for producing the conventional membranes and patches can be lengthy and costly. The resultant membranes and patches are also not standardized and are difficult to consistently replicate. It has been found that the properties of the membranes and patches are highly dependent on the operator.

The conventional membranes and patches have also been found to be not efficient for wound healing. The membranes and patches are not produced in a safe, contamination free environment (i.e. in a closed circuit). As a result, the membranes and patches which are conventionally used for wound healing have a low benefit to risk ratio.

There is therefore a need for a standardized, reproducible, efficient and safe wound membranes which overcomes the above drawbacks of conventional membranes and patches. There is a need for a simple, economical and sterile (i.e. closed to the atmosphere) container and process for quickly producing standardized, replicable, efficient and safe wound membranes.

DESCRIPTION

Figure 1A:
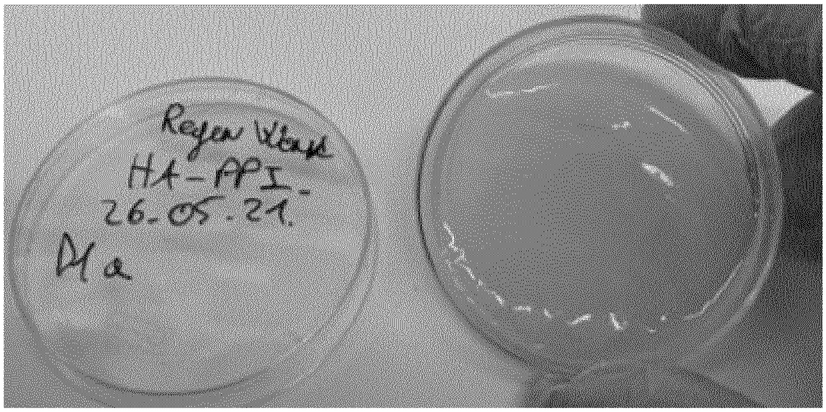
FIGS. 1*a* to 1*c* are photographs illustrating topical gels for topical application onto or into wounds obtained using Platelet-Rich Plasma obtained from Donor 1 and a container and method according to embodiments of the present invention.

The present invention provides containers, kits and methods for the safe and effective preparation of isolated plasma derived products or bone marrow derived products which are useful for use as a drug/medicament, or for treating wounds and for improved wound healing.

The invention provides highly innovative, efficient, specific and reproducible containers to rapidly produce standardized preparations of Platelet Rich Plasma (PRP) or Bone Marrow Concentrate (BMC) for forming a topical gel or topical membrane or topical patch for use in wound healing.

The invention comprises methods, containers and tubes intended for rapid, efficient, reliable, reproducible and standardised preparation of Platelet-Rich Plasma (PRP) or Bone Marrow Concentrate (BMC) from a donor's blood or bone marrow for formation of a topical gel or topical membrane or topical patch for use in wound healing treatment.

According to a first aspect of the present invention there is provided a container for use in the preparation of a topical gel or topical membrane or topical patch formed from a Platelet Rich Plasma (PRP) or Bone Marrow Concentrate (BMC)-coagulation activator combination, in which the container is prefilled with or comprises at least one thixotropic gel and a composition comprising at least one coagulation activator.

According to a second aspect, the present invention provides a container for use in the preparation of a topical gel or topical membrane or topical patch formed from biomaterial, and a Platelet-Rich Plasma (PRP) and/or bone marrow concentrate (BMC)-coagulation activator combination, in which the container is prefilled with or comprises an anticoagulant, a thixotropic gel, and a composition comprising at least one coagulation activator and at least one biomaterial.

The container is preferably a centrifugation tube or centrifugation syringe. The container is preferably a centrifugation tube closed to the atmosphere.

Preferably, the container is made of borosilicate. Preferably, the container contains silicone, and is depyrogenated. The containers may for example be coated with one or more substances, preferably silicone. The container or tube preferably comprises glass, modified polyamide (MPA) or polyethylene terephthalate. The container or tube may be substituted and/or combined with synthetic copolymers, ceramic and glass-ceramics, bioartificial blends of natural and synthetic materials.

The container or tube preferably has a layered structure with an interior wall comprising polypropylene or internal coating.

The container or tube preferably comprises glass, modified polyamide (MPA) or polyethyleneterephthalate (PET) and an interior wall comprising polypropylene.

The container or tube preferably includes a stopper comprised of butyl rubber or halo butyl rubber having a hardness of 40-60 Shore A. The tube preferably has a shelf life with stable vacuum of 18-24 months.

The container or tube is preferably under vacuum, for example is a vacuum tube. In the alternative, the container or tube is preferably not a vacuum tube.

Preferably, the container is under vacuum with a stopper. A container is herein characterized by a distal end and proximal end, with the proximal end having an aperture for the collection of material, substance or composition, e.g. whole blood or bone marrow.

The container optionally contains two or more chambers. Each chamber may be prefilled with or contain or be configured to contain in use: a substance (such as for example an anticoagulant), one or more biomaterial(s), cell extract, platelet rich plasma, bone marrow concentrate, and/or the composition comprising the coagulation activator. The contents of each chamber may be isolated from the contents of the other chamber(s) prior to use, and wherein the contents of the chambers may optionally enter into contact with each other or be mixed together inside or outside of the container, wherein said chambers are preferably separated by a chemical or biological substance, membrane or any other means of separation within the container, wherein such means of separation may optionally disintegrate over time or is biodegradable.

The container according to any of the aspects of the invention may be suitable for:

- i) collection of PRP and/or BMC, from a collection device, preferably or optionally a collection holder, wherein said transfer optionally occurs in closed circuit, preferably or optionally automatically, preferably or optionally by vacuum, preferably or optionally either by direct contact between the the container and the collection device, and/or
- ii) centrifugation, and/or
- iii) collection or transfer of said PRP and/or BMC in combination with at the least one biomaterial into another device, preferably or optionally syringe, preferably or optionally in closed circuit, preferably or optionally automatically, and/or
- iv) optionally mixing and/or inversion; and/or
- v) optionally topical application of said PRP or BMC-coagulation activator combination (optionally with at the least one biomaterial) on or into a human or animal, preferably or optionally in closed circuit, preferably or optionally automatically.

The container according to any of the aspects of the invention may for example be a syringe:

- a) said syringe comprises or is prefilled with or comprises at least one thixotropic gel and a composition comprising at least one coagulation activator, and optionally at least one biomaterial selected from hyaluronic acid, chitosan, silk protein or fibroin, cell extract or any combination thereof,
- b) optionally a collection device, preferably or optionally a collection holder, can be affixed to said syringe for the collection of PRP or BMC into said syringe,
- c) optionally the coagulation activator is selected from thrombin serum, calcium gluconate and/or calcium chloride,
- d) said syringe optionally contains two or more chambers wherein each chamber may contain a substance, biomaterial, cell extract, PRP or BMC, and coagulation activator, wherein the contents of each chamber are isolated from each other in their respective chamber and wherein said compositions may optionally enter into contact with each other or be mixed together inside and or outside said syringe, wherein said chambers are separated by a chemical or biological substance, membrane or any other means of separation, wherein such means of separation may optionally disintegrate over time or is biodegradable, and may be suitable for:

- i) collection of PRP and/or BMC, from a collection device, preferably or optionally a collection holder, wherein said transfer optionally occurs in closed circuit, preferably or optionally automatically, preferably or optionally by vacuum, preferably or optionally either by direct contact between the the container and the collection device, and/or
- ii) optionally inversion, and/or
- iii) optionally topical application of said PRP or BMC-coagulation activator combination (optionally with at the least one biomaterial) on or into a human or animal, preferably or optionally in closed circuit, preferably or optionally automatically.

The thixotropic gel is preferably a large polymer complex with mode of action dependent on viscosity and density.

The thixotropic gel is preferably selected from: an oligomer, polymer, polyolefin hydrocarbon oligomer, polyester gel, an acrylic resin mixture, a PEG-Silica Gel, a polyoxyalkylene polyol, trioctyl trimellitate, a hydrocarbonated resin, silica dimethyl silylate, or any combination thereof.

In one embodiment, the thixotropic gel is a polyoxyalkylene polyol. The polyoxyalkylene polyol preferably comprises hydroxyl group containing groups of formula 1:

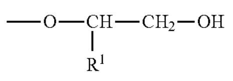

(1)

The polyoxyalkylene polyol may be selected from one or more of: polyethylene and/or polypropylene glycol trimethylolpropane ether, methyloxirane polymer with oxirane, ether with 2-ethyl-2-(hydroxymethyl)-1,3-propanediol; poly (oxyethylene and/or oxypropylene)trimethylolpropane ether, trimethylol propane, ethoxylated trimethylolpropane, propxylated trimethylol propane, or any combination thereof. Preferably, the thixotropic gel is trioctyl trimellitate. Preferably, the thixotropic gel is a hydrocarbonated resin. Preferably, the thixotropic gel is silica dimethyl silylate.

Use of a thixotropic gel as described herein, preferably use of a polyoxyalkylene polyol, enables the collection of a plasma concentrate with very good stability. Furthermore, the time required for preparation is significantly less compared to conventional thixotropic gels and produces plasma concentrates with improved results compared to the use of conventional thixotropic gels.

The thixotropic gel may contain additional substances such as, or equivalent thereof, Tris(2-ethylhexyl)benzene-1, 2,4-tricarboxylate, silicon dioxide, silane, dichlorodimethyl-reaction products, and/or silica. The thixotropic gel may be further characterized by: insoluble in water, partially soluble in acetone, and easily soluble in hexane. Further, the thixotropic gel may be characterized by a viscosity of approx. 400 to 700 Pa·s at 15° C., approx. 100 to 250 Pa·s at 25° C., 30 to 100 Pa·s at 45° C. and 10 to 80 Pa·s at 65° C.

The thixotropic gel may comprise trioctyl trimellitate, silica, hydrocarbon resin, polyol, phenol(s) and phosphite ester.

In some embodiments, the trioctyl trimellitate is Tris (2 ethyhexyl), said silica is Dimethyl dichlorosilane, said hydrocarbon resin is Cycloaliphatic hydrocarbon Resin, said polyol is Polyalkylene Polyol, said phenol(s) is Tetrakis(3-(3,5-di-tert-butyl-4-hydroxyphenyl) propionate of pentaerythritol) and said phosphite ester is Phosphite of tris(2, 4-di-tert-butylphenyle).

In some embodiments, the thixotropic gel comprises trioctyl trimellitate in the range of 40-60%, silica in the range of 2-10%, hydrocarbon resin in the range of 30-60%, polyol in the range of 1-5%, phenol(s) in the range of 0-1% and phosphite ester in the range of 0% to 0.06%.

In some embodiments, the thixotropic gel comprises trioctyl trimellitate at about 50.96%, silica at about 4.21%, hydrocarbon resin at about 43%, polyol at about 1.73%, phenol(s) at about 0.05% and phosphite ester at about 0.05%.

In some embodiments, the thixotropic gel comprises trioctyl trimellitate in the range of 35-55%, silica in the range of 2-10%, hydrocarbon resin in the range of 20-40%, azelate esters in the range of 10-30%, and phenol(s) in the range of 0-1%.

In some embodiments, the thixotropic gel comprises trioctyl trimellitate at about 50.96%, silica at about 4.21%, hydrocarbon resin at about 43%, azelate esters at about 15.82%, and phenol(s) at about 0.05%.

The thixotropic gel may comprise trioctyl trimellitate, silica, hydrocarbon resin, phenol(s) and phosphite ester.

In some embodiments, the silica is dimethyl dicholorsilane and/or the hydrocarbon resin is cycloaliphatic hydrocarbon resin and/or the phenol is Tetrakis(3-(3,5-di-tert-butyl-4-hydroxyphenyl) propionate of pentaerythritol) and/or the phosphite ester is tris(2,4-di-tert-butylphenyl) phosphite.

In some embodiments, the thixotropic gel comprises trioctyl trimellitate in the range of 40-60%, silica in the range of 2-10%, hydrocarbon resin in the range of 30-60%; phenol(s) in the range of 0-1%, and phosphite ester in the range of 0% to 0.06%.

In some embodiments, the thixotropic gel comprises trioctyl trimellitate at about 52.26%, silica at about 7.99%, hydrocarbon resin at about 39.65%, phenol(s) at about 0.05%, and phosphite ester at about 0.05%.

Preferably, the thixotropic gel is characterized by a density selected from about 1.04 $g/cm^3$ to about 1.095 $g/cm^3$.

In another aspect of the invention is provided a container (tube or syringe) only prefilled with or comprising:

i) a thixotropic gel and anticoagulant, or ii) a thixotropic gel.

Preferably, the coagulation activator comprises a thrombin activator and/or a fibrinogen activator and/or thrombin and/or an autologous thrombin and/or an autologous thrombin serum and/or calcium chloride and/or calcium gluconate and/or calcium saccharate.

Preferably, the coagulation activator is selected from: thrombin serum, calcium gluconate, calcium chloride, calcium saccharate or a combination thereof. Preferably, the coagulation activator is selected from: thrombin serum, calcium gluconate, calcium chloride, or a combination thereof.

Preferably, the coagulation activator comprises a calcium salt, such as for example, without limitation, $CaCO_3$, $CaSO_4$ or $CaCl_2$) The coagulation activator is preferably calcium gluconate (CaGL). In one embodiment, the coagulation activator, for example calcium gluconate, at least about 5%, for example at least about 6%, at least about 7%, at least about 8%, at least about 9%, at least about 10% (compared to the PRP or BMC volume) may be added in the container (tube). Preferably, the coagulation activator, for example calcium gluconate, is present in an amount of about 10% compared to the PRP or BMC volume. Preferably, the coagulation activator, for example calcium gluconate, at no more than about 20% (compared to the PRP or BMC volume) may be added in the container (tube). Preferably, the coagulation activator, for example calcium gluconate at between about 5% and about 20%, preferably between about 6% and about 20%, preferably between about 6% and about 15%, for example about 10% (compared to the PRP or BMC volume) may be added in the container (tube). More preferably, calcium gluconate at about 10% (compared to the PRP or BMC volume) is added in the container (tube). For example, for a 100 ml of solution of coagulation activator about 9 g of Calcium gluconate may be used with for example PPI water.

The coagulation activator(s) may be provided in solution, and may be filtered using a filter to remove any particles. The grade of filter may be selected by a person skilled in the art depending on the particular requirements. In one embodiment, the filter is an about 0.22 μm filter.

In one preferred embodiment, the composition comprising the at least one coagulation activator is located beneath the thixotropic gel, or at a more distal end of the container (tube) than the thixotropic gel. For example, the coagulation activator(s) may be provided as a layer located beneath the thixotropic gel, or at a more distal end of the container (tube) than the thixotropic gel.

In one embodiment, the coagulation activator may be added as a second layer above the thixotropic gel layer in the container (tube). If the container (tube) further comprises at least one anticoagulant, the coagulation activator is kept separate from the at least one anticoagulant.

In one embodiment, calcium chloride or calcium saccharate may be used as a coagulation activator.

In one embodiment, a combination of calcium gluconate and calcium saccharate may be used. For example, for a 100 ml of solution of coagulation activators (calcium gluconate and calcium saccharate), about 9.5 g of Calcium gluconate and about 360 mg of Calcium saccharate may be used. For example, for a 100 ml of solution of coagulation activators (calcium gluconate and calcium saccharate), about 9.5 g of calcium gluconate and about 360 mg of calcium saccharate may be used. For example, for a 2 ml single dose ampoule about 0.19 g of calcium gluconate and about 7.2 mg calcium saccharate may be used for a calcium content of about 0.463 mmol per 2 ml ampoule. For example, for a 5 ml single dose ampoule, about 0.47 g of calcium gluconate and about 18 mg calcium saccharate may be used for a calcium content of about 1.148 mmol per 5 ml ampoule. The skilled artisan will easily determine the appropriate calcium content according to the specific use. The solution is preferably PBS free, for example comprises PPI water.

It is to be understood that the container may comprise a combination of coagulation activators in order to provide a PRP or BMC coagulation activator combination with predetermined stiffness.

The container may further comprise or is further prefilled with at least one additional biomaterial. The composition may further comprise at least one additional biomaterial. The at least one biomaterial may be selected from one or more of: hyaluronic acid, chitosan, silk protein or fibroin or any combination thereof. For example, the at least one additional biomaterial may be hyaluronic acid.

Hyaluronic acid may be in the form of a gel.

The hyaluronic acid is preferably reticulated or non-reticulated.

The hyaluronic acid may be non-crosslinked or crosslinked. Preferably, the hyaluronic acid has a molecular weight of about 1500 Kda and is present at about 1.5% to about 2.5%, preferably 1.5% to about 2%, preferably about 2%. The hyaluronic acid may be a crosslinked hyaluronic acid obtained from a method herein described. The molecular weight might range from about 500 KDa to about 9000 KDa. The hyaluronic acid preferably has a molecular weight of about 1550 kda.

In one embodiment, the container may contain about 40 mg to about 200 mg hyaluronic acid.

The container may contain from about 1 ml to about 5 ml of hyaluronic acid.

In one preferred embodiment, the at least one biomaterial comprises hyaluronic acid and the at least one coagulation activator comprises calcium gluconate.

Preferably, the composition comprising the at least one coagulation activator and the at least one biomaterial form a single layer or composition.

The at least one coagulation activator and the at least one biomaterial are preferably located beneath the thixotropic gel, or at a more distal end of the container than the thixotropic gel.

In one embodiment, the composition further comprises water or water for injection (i.e. ultra pure water: 0 mOsmol $kg^{-1}$ or about 0 mOsmol $kg^{-1}$) located beneath the thixotropic gel, or at a more distal end of the container than the thixotropic gel.

In one embodiment, the single layer or composition further comprises water or water for injection (i.e. ultra pure water: 0 mOsmol $kg^{-1}$ or about 0 mOsmol $kg^{-1}$).

The container is preferably Phosphate-buffered saline (PBS) free. The composition is preferably Phosphate-buffered saline (PBS) free. For example, the hyaluronic acid may be Phosphate-buffered saline (PBS) free, (i.e. does not comprise PBS).

The term "Phosphate-buffered saline (PBS) free" is used herein to mean that the container, tube or composition comprises less than about 0.5% wt, preferably less than about 0.1% wt, preferably less than about 0.05% wt, preferably less than about 0.01% wt of the or each component of the composition, or of the composition, or of the container or tube.

The container preferably comprises about 2 ml of hyaluronic acid-calcium gluconate combination (HA-Ca-Glu) within the tube. The calcium gluconate provided by the combination is preferably present within the container in an amount of about 3%, about 6%, about 10%, about 13%, about 16%, or about 20% of calcium gluconate in relation to the volume of PRP or BMC within the container, or in a range of about 3% to about 20%, or about 6% to about 16% of calcium gluconate in relation to the volume of PRP or BMC within the container.

In one embodiment, the container, for example a tube (125 mm), comprises or is prefilled with about 2 g of a composition comprising hyaluronic acid-calcium gluconate (HA-CaGlu) gel, about 3 g of thixotropic gel, and about 0.6 ml of sodium citrate with about 6 ml of vacuum. The composition comprising hyaluronic acid-calcium gluconate is preferably PBS-free. The composition comprising hyaluronic acid-calcium gluconate is preferably provided at a concentration of about 0.3 ml of calcium gluconate for about 40 mg hyaluronic acid (HA).

In one embodiment, the container, for example a tube, comprises about 3 ml of Platelet rich plasma and about 2 ml of hyaluronic acid-calcium gluconate combination (HA-CaGlu) within the tube. The container preferably contains about 10% of calcium gluconate compared to the volume of platelet rich plasma According to a further aspect, there is provided a method of producing a PBS free-coagulation activator-biomaterial mixture, the method comprising:

a) mixing at least one coagulation activator with PBS-free water (for example with PPI water) to obtain a PBS-free coagulation activator solution; and
b) mixing the PBS-free coagulation activator solution with at least one biomaterial to obtain a PBS-free coagulation activator-biomaterial solution.

The method may further comprise using a filter to remove any particles. The grade of filter may be selected by a person skilled in the art depending on the particular requirements. In one embodiment, the filter is an about 0.22 μm filter. The method may comprise filtering the one or more of: the PBS-free coagulation activator solution and/or the PBS-free coagulation activator-biomaterial solution, The coagulation activator is preferably calcium gluconate and the biomaterial is preferably hyaluronic acid.

Preferably, the container may further comprise or further prefilled with or comprises or comprises at least one anticoagulant. The at least one anticoagulant may be located (proximal) above the thixotropic gel (distal), or at a more proximal end of the container than the thixotropic gel.

The system may further comprise an anticoagulant selected from the group consisting of buffered citrate, acid citrate dextrose (ACD), modified ACD, heparin and heparin salts, ethylenediaminetetraacetic acid (EDTA) and salts thereof, iodo acetate salts, oxalate salts, fluoride salts as water solution or lyophilized material wet or dry sprayed on the collection tube inner wall, wherein said anticoagulant is residing in or adapted to be added to said collection tube.

Preferably, the anticoagulant is selected from sodium citrate. Preferably, the anticoagulant, for example sodium citrate, is present at a concentration of about 0.1 M.

The anticoagulant in all the above devices may be at a concentration different than about 0.1M, ranging from about 0.05 to about 0.15M, or preferably from about 0.08M to about 0.14M, or greater than about 0.08M, preferably greater than about 0.09M.

The densities provided (may be referred to as gravity) have been measured at a temperature of about 25° C.

According to a third aspect of the present invention, there is provided a container as herein described, wherein the topical gel or topical membrane or topical patch comprises either i) Platelets and biomaterial
ii) Stem cells or bone marrow stem cells and biomaterial.
iii) Platelets, stem cells and biomaterial.

According to a fourth aspect of the present invention, there is provided a container as herein described for use in the preparation of a topical gel or topical membrane or topical patch formed from a Hyaluronic Acid, and a Platelet Rich Plasma (PRP) and/or bone marrow concentrate (BMC)-coagulation activator combination, in which the container comprises or is prefilled with or comprises:

a) an anticoagulant,
b) a thixotropic gel characterized by a density selected from about 1.04 g/$cm^3$ to about 1.95 g/$cm^3$, and a composition comprising:

c) hyaluronic acid, and
b) a coagulation activator, wherein said thixotropic gel is provided as a layer positioned above the composition comprising hyaluronic acid and coagulation activator from the distal end of said container, in which the composition comprising hyaluronic acid and coagulation activator is mixed together within a single layer prior to filling the tube (but may be mixed in the tube), and in which the anticoagulant is provided as a further layer positioned above the layer of thixotropic gel from the distal end of said container.

According to a further aspect, the present invention provides a container or tube as herein described, according to any of the aspects of the invention, or a platelet rich plasma (PRP) and/or bone marrow concentrate (BMC)-coagulation activator combination for topical use (for example for use in the preparation of a topical gel or topical membrane or a topical patch) prepared according to a method as herein described further comprising or further prefilled with or comprises one or more of: thrombin serum, tricalcium phosphate (TCP), a bone substitute, hyaluronic acid composition, calcium gluconate, calcium saccharate, chitosan, fibroin, fibroin-silk protein or fibroin proteins, growth factors, mannitol, collagen, albumin, ascorbic acid, cream, fat cells, fat tissue, bone marrow concentrate, lubricin, cd-gelatin, botulinum toxin and/or one or more cell extracts, optionally or preferably an autologous cell extract, selected from an extract of keratinocytes, bone marrow, fibroblasts, periosteum or corneal cells, melanocytes and Langerhans cell, fat cells, muscle cells such as myoblasts and satellite cells, osteoblasts, chondrocytes, umbilical cord cells, stem cells, mesenchymal stem cells (MSCs), preadipocytes, pre-endothelial cells, Schwann cells or Achilles tendon cells, or any combination thereof.

Advantageously, the containers of the invention do not induce an inflammatory reaction and avoid/reduce reactions to plasma/serum constituents, including immunological reactions such as serum sickness.

According to a further aspect, the present invention provides an isolated plasma-derived product or bone marrow-derived product obtained using a container or tube as herein described.

The isolated plasma-derived products or bone marrow-derived products are preferably for use as drug/medicament, or for example for use in wound healing or for use as a topical gel, topical membrane or topical patch or wound dressing. In one embodiment, the topical membrane is suturable.

The isolated plasma derived product or bone marrow-derived product preferably has a pH of around 7, for example at least about 6.5 and no more than about 7.5, for example in the range of about 7.0 to about 7.5, for example about 7.4.

The isolated plasma derived product or bone marrow derived product preferably has an osmolarity in the range of between about 280 to about 330 mOsm, preferably in the range of about 290 to about 320 mOsm, preferably in the range of about 300 to about 310 mOsm.

The isolated plasma or bone marrow derived product obtained using a container or tube as herein described preferably has an increased platelet count (per ml of extracted blood) compared to the platelet count of isolated plasma or bone marrow derived products obtained using conventional devices.

Preferably, the container comprises or is prefilled with thixotropic gel and at least one anticoagulant, for example sodium citrate.

In one embodiment, the isolated plasma or bone marrow derived product has a platelet count of at least about 145000, preferably at least about 150000, for example about 154000 platelet count per ml of extracted blood.

In one embodiment, the topical gel, membrane or patch formed using a container of the present invention has improved adherence properties for surfaces, in particular for wound surfaces (i.e. skin and surrounding tissue) compared to conventional wound dressing membranes. In one embodiment, the topical gel, membrane or patch formed using a container of the present invention remains adhered to the contact surface (for example skin and surrounding tissue) when inverted without any substantial change to the shape/form of the gel, membrane or patch. The present invention can therefore be used to provide membranes with improved adherence for wounds and as such will remain in place providing improved protection.

According to a further aspect, the present invention provides a system for collecting a Plasma-Rich Platelet (PRP) and/or bone marrow concentrate (BMC)-coagulation activator combination for use in the preparation of a topical gel or topical membrane or topical patch, the system comprising:

a container or tube as herein described, in which the container or tube has at least one stopper for maintaining said container or tube closed to the atmosphere;

optionally a syringe adapted to remove platelet poor plasma (PPP) or a cellular fraction depleted in stem cells from said container or tube after centrifugation optionally a collection syringe adapted to collect plasma enriched in platelets or a cellular fraction enriched in stem cells from said container or tube after centrifugation; and optionally at least one needle for attaching to the collection syringe and adapted to be received in the collection tube while said container or tube remains closed to the atmosphere.

The system may further comprise a vessel containing an agent selected from the group consisting of hyaluronic acid, thrombin, $CaCl_2$), collagen, allograft bone, autograft bone, bone substitute, autologous adult stem cells, adenine diphosphate (ADP), and any combination thereof configured for mixing with plasma enriched with platelets or cellular fraction enriched in stem cells.

The filter may have a pore size adapted to reject a portion of white blood cells or cellular fraction enriched in stem cells.

The invention encompasses the following combinations (whether in fresh, lysate or else form), but not limited to:

i) plasma concentrate from blood+bone marrow concentrate, ii) plasma concentrate from blood+serum from bone marrow, iii) plasma concentrate from blood+serum from blood, iv) bone marrow concentrate+serum from bone marrow, v) Cbone marrow concentrate+serum from blood, or vi) serum from bone marrow+serum from blood.

According to a further aspect, there is provided a kit comprising one or more containers as herein described. The kits may comprise any number and combination of containers/tubes herein disclosed, for example with a number of containers/tubes ranging from 1 to 1000. Furthermore, the kits may contain one or more of the following additional material:

Blood collection accessory set

Horizontal head (swinging bucket) or a fixed 45° angle rotor centrifuge.

The containers, tubes or syringes may be of different shapes and made of crystal, glass, plastic or metal. Preferably, the containers, tubes or syringes are made of plastic, preferably COP or COC, preferably without phthalates.

The centrifuge is preferably adapted to centrifuge said container or tube at about 300 to about 2000 g, preferably at about 1500 g.

The kit may further comprise:

i) a collection device, optionally or preferably comprising or consisting of a collection holder with accessories, preferably or optionally a safety lock and butterfly needle, to be affixed to the container for collection of blood and/or bone marrow into said container and wherein said collection preferably or optionally occurs in closed circuit, preferably or optionally automatically, preferably or optionally by vacuum, and/or ii) a collection device to be affixed to the container for collection of PRP and/or BMC, wherein said collection preferably or optionally occurs in closed circuit, preferably or optionally automatically, and/or iii) a transfer device to be affixed to the container for the transfer of PRP and/or BMC into another container, wherein said container is preferably or optionally a tube or syringe, preferably or optionally under vacuum, wherein said transfer preferably or optionally occurs in closed circuit, preferably or optionally automatically, preferably or optionally by vacuum, preferably or optionally either by direct contact between the two containers or through means of a device, and/or iv) optionally wherein said device further comprises at least one filter (PALL OR DSELF-TRAINER) or substance for the separation of other blood components and/or bone marrow components, in order to remove cells from the PRP and/or BMC, and/or v) the container optionally is under vacuum.

vi) the container may contain a filter for the removal of cells. Such filter may instead or in addition be present in a syringe, other device or a cell strainer for the collection of the PRP and/or BMC.

The kit may further comprise a syringe-driven filter for collecting plasma from one or more of the containers or tubes as herein described. The syringe-driven filter is preferably operable to be in fluid communication with the one or more containers or tubes as herein described. The syringe-driven filter preferably comprises a PVDF membrane filter. The syringe-driven filter preferably comprises a 0.55 μm or lower membrane filter. For example, the membrane filter may have a membrane size of 0.55 μm, 0.54 μm, 0.53 μm,0.52 μm, 0.51 μm, 0.50 μm, 0.49 μm, 0.48 μm, 0.47 μm, 0.46 μm, 0.45 μm or lower. Preferably the membrane filter has a membrane size of 0.45 μm or lower. It has been found that membrane size of larger than 0.55 μm leads to too great contamination levels. It has also been found that a membrane size of 0.45 μm or less provides no contamination. The membrane filter may be in the syringe to collect the plasma. The membrane filter may be in the container or tube. The membrane filter may be in the container or tube and located either above or below the thixotropic gel. The membrane filter may be in both the syringe and the container or tube. For example, the syringe may comprise a first membrane filter and the container or tube may have a second membrane filter. A first membrane filter may be provided in a first syringe and a second membrane filter may be provided in a second syringe. The first and second syringes may be used consecutively. The first membrane filter may have a different membrane size to the second membrane filter. For example, the first membrane filter may have a larger membrane size, for example 0.5 μm, than the second membrane filter, which may for example have a size of 0.45 μm.

For topical use, in the case of wounded patient (chronic wound, surgical wound), the container (tube or syringe) of the present invention may further contain or further prefilled with or comprises a preservation solution (such as for example a PC or BMC preservation), optionally or preferably plasmalyte-A, thrombin serum, tricalcium phosphate (TCP), calcium saccharate, chitosan, fibroin, fibroin-silk protein or fibroin proteins, growth factors, mannitol, collagen, albumin, or ascorbic acid.

In further embodiments, the invention provides a container (or tube or syringe) according to any of the previous aspects or embodiments further characterized in that:

a) at the least two containers, at the least one container and one syringe or at the least two syringes may be connected together through means of a connecting device enabling transfer of any substance, material, plasma, serum or else composition from one container or syringe to the other container or syringe, b) said container is a tube, and/or c) said tube or syringe allows the withdrawal of about 1 ml to about 20 ml of whole blood, bone marrow, plasma, serum, preferably or optionally about 2 ml to about 10 ml, preferably or optionally about 4 ml.

d) said container and/or syringe is sterile and/or non-pyrogenic, and/or e) said container is suitable for the preparation of PRP or BMC, and/or f) said container is prefilled with or comprises or comprises from about 1 ml to about 10 ml of thixotropic gel, and/or g) said container comprises or is prefilled with or comprises about 0.2 ml to about 10 ml of at least one coagulation activator, preferably calcium gluconate, preferably from about 1% to about 20%;

h) said container optionally further comprises or is prefilled with or comprises at least one anticoagulant, preferably with about 0.2 ml to about 10 ml of at least one anticoagulant, preferably sodium citrate, from about 2% to about 6%, preferably or optionally about 4%, and/or i) said container is prefilled:
   1. during the manufacturing process and/or
   2. before centrifugation, either before and/or after collection of blood or bone marrow into said container, and/or
   3. with a thixotropic gel and the composition comprising at least one coagulation activator, optionally further comprising at least one biomaterial and/or anticoagulant, or any combination thereof and is contained in a kit or medical device.

In further embodiments, the invention provides a container, tube or kit according to any of the previous aspects or embodiments, further comprising a piston stopper, at the least one self-adhesive disc, a luer connector, anesthetic solution, injection accessories such as needles and/or syringes, luer-lock syringes, a clip device, a trocar, ampoule of coagulation activator such as calcium chloride or calcium gluconate, a paper mask, a nozzle for spray application, a double piston stopper, an applicator syringe holder and/or a connector, or any combination thereof.

In one embodiment, the container of the present invention is able to be used to provide a PRP or BMC-coagulation activator combination which maintains the low viscosity of hyaluronic acid despite the presence of the coagulation activator. This maintenance of low viscosity of the combination (in the presence of the coagulation activator) has been achieved due to replacing PBS with PPI water during the preparation of hyaluronic acid.

The PRP or BMC-coagulation activator combinations of the present invention combine the beneficial effects of PRP or BMC and hyaluronic acid whilst providing a standardized topical gel or membrane or patch for the treatment of chronic wounds.

In another aspect, the invention provides a method of automatically manufacturing containers or tubes by means of a filling machine comprising controlled vacuum and clogging of the containers or tubes for filling the thixotropic gel and the composition comprising the at least one coagulation activator, optionally further filling with at least one anticoagulant and/or at least one biomaterial such as hyaluronic acid.

Manufacturing of the container or use of the container of the present invention is preferably performed under laminar flow and/or bioburden controlled.

According to a further aspect, the present invention provides a method for obtaining a Platelet-Rich Plasma (PRP) and/or bone marrow concentrate (BMC)-coagulation activator combination using a system as herein described, comprising:

- filling the container or tube with whole blood or a first cellular fraction that includes stem cells;
- inverting the container or tube to homogenize the contents;
- centrifuging the container or tube to separate red blood cells from plasma enriched in platelets, or to separate a fraction depleted in stem cells from a fraction enriched in stem cells; and
- inverting the centrifuged container or tube to homogenize the contents.

According to a further aspect of the present invention, there is provided a method for the preparation of a topical gel or topical membrane or topical patch formed from a platelet-rich plasma (PRP) and/or bone marrow concentrate (BMC)-coagulation activator combination, comprising the steps of:

- filling the container or tube with whole blood or a first cellular fraction that includes stem cells;
- optionally inverting the container or tube to homogenize the contents;
- centrifuging the container or tube to separate red blood cells from plasma enriched in platelets, or to separate a fraction depleted in stem cells from a fraction enriched in stem cells;
- optionally inverting the centrifuged container or tube to homogenize the contents; and
- collecting the PRP and/or bone marrow concentrate (BMC)-coagulation activator combination to provide or for use as a topical gel or topical membrane or topical patch.

The PRP and/or bone marrow concentrate (BMC)-coagulation activator combination is preferably collected in a separate container, for example by transferring (e.g. pouring) the PRP and/or bone marrow concentrate (BMS) into a separate container.

Preferably, the preparation involves only one centrifugation. The preparation comprises a combination of centrifugation and homogenization to ensure that coagulation occurs after centrifugation to provide a homogenous topical membrane, patch or gel.

The first homogenization step is required to be performed or is a recommended step in order to ensure that coagulation does not occur prior to the centrifugation step.

The second homogenization step is required to be performed or is a recommended step to ensure that a homogenous membrane or patch or gel is produced in the separate container.

Preferably, the centrifugation step is performed at a force of or about 1500 g (this speed is with a radius of about 20 cm at about 2500). Preferably, the centrifugation step is performed in a sufficient length of time to form a barrier between the plasma and the gel containing the erythrocytes. Preferably, centrifugation time is about 1 minute up to about 10 minutes, preferably about 5 minutes. In one preferred embodiment, centrifugation speed is about 1500 g with centrifugation time of about 5 minutes. Centrifugation time and speed depends on the formulation present in the device. The skilled artisan can determine the appropriate centrifugation time and speed according to the composition used.

Preferably, the centrifugation step is performed at a force of about 1500 g for approximately 5 minutes.

The centrifugation preferably results in platelet enrichment in a platelet enriched plasma of about 1.5 to about 10 times compared to said whole blood.

The method may further comprise the step of letting the Platelet-Rich Plasma (PRP) and/or bone marrow concentrate (BMC)-coagulation activator combination rest in a separate container until formation of the topical gel or topical membrane or topical patch.

The Platelet-Rich Plasma (PRP) and/or bone marrow concentrate (BMC)-coagulation activator combination is preferably left to rest for a period of about 5 minutes to about 20 minutes.

In some embodiments, the plasma or serum is preferably autologous or homologous.

In some embodiments, the plasma, serum or both are frozen for storage and thawed prior to administration of the plasma/serum to the subject. In some embodiments, the plasma, serum or both are lyophilized for storage and reconstituted prior to administration of the plasma/serum to the subject.

The method may comprise withdrawing a portion of platelet poor plasma or a cellular fraction reduced in stem cells with a second syringe after centrifugation and before obtaining said plasma enriched in platelets or cellular fraction enriched in stem cells.

According to a further aspect, there is provided a system for use in the preparation of a topical gel or topical membrane or topical patch formed from a PRP or BMC-coagulation activator combination, in which the system comprises:

a) a first container for the preparation of PRP or BMC comprising or prefilled with at least one thixotropic gel, and optionally an anticoagulant; and b) a second container comprising or prefilled with a composition comprising at least one coagulation activator (preferably calcium gluconate) and optionally at least one biomaterial (for example hyaluronic acid).

The second container preferably comprises at least one biomaterial, for example hyaluronic acid, together with water for injection, preferably PBS free.

According to a further aspect, there is provided a method for the preparation of a topical gel or topical membrane or topical patch formed from a PRP and/or bone marrow concentrate (BMC)-coagulation activator combination using a system as herein described, comprising:

a) centrifuging once only whole blood or bone marrow in a first container of the system; and b) collecting platelet rich plasma or bone marrow concentrate from the first container and introducing the platelet rich plasma or bone marrow concentrate into a second container and mixing with the at least one coagulation activator and optionally at least one biomaterial contained therein, preferably a coagulation activator and a biomaterial as single composition or in different layers, preferably PBS free, preferably further comprising or prefilled with water for injection.

According to a further aspect, there is provided a system for use in the preparation of a topical gel or topical membrane or topical patch formed from a PRP or BMC-coagulation activator combination, in which the system comprises:

a) a first container for the preparation of PRP or BMC comprising or prefilled with at least one thixotropic gel, and optionally an anticoagulant;

b) a second container comprising or prefilled with a composition comprising at least one coagulation activator (preferably calcium gluconate); and c) a third container comprising or prefilled with at least one biomaterial (for example hyaluronic acid).

The third container preferably comprises or prefilled with at least one biomaterial, for example hyaluronic acid, together with water for injection, preferably PBS free.

According to a further aspect, there is provided a method for the preparation of a topical gel or topical membrane or topical patch formed from a PRP and/or bone marrow concentrate (BMC)-coagulation activator combination using a system as herein described, comprising:

a) centrifuging once only whole blood or bone marrow in a first container of the system;

b) collecting platelet rich plasma or bone marrow concentrate from the first container and introducing the platelet rich plasma or bone marrow concentrate into a second container and mixing with the at least one coagulation activator;

c) collecting platelet rich plasma or bone marrow concentrate-coagulation activator(s) combination from the second container and introducing the mixture into a third container and mixing with the at least one biomaterial contained therein.

The method preferably comprises mixing the plasma enriched with platelets or cellular fraction enriched in stem cells with an agent selected from the group consisting of hyaluronic acid, thrombin, $CaCl_2$), collagen, allograft bone, autograft bone, bone substitute, autologous adult stem cells, adenine diphosphate (ADP), and any combination thereof.

According to a further aspect, there is provided a sterilized, vacuum-sealed separator tube for preparing a Platelet Rich Plasma (PRP) and/or bone marrow concentrate (BMC)-coagulation activator combination for use in the formation of a topical gel or topical membrane or topical patch from whole blood comprising:

an inlet adapted to introduce whole blood;

a thixotropic gel suitable for preparing a topical gel or topical membrane or topical patch; and a composition comprising at least one coagulation activator, wherein the thixotropic gel forms a barrier between the Platelet Rich Plasma (PRP) and/or bone marrow concentrate (BMC)-coagulation activator combination and red blood cells.

Preferably, the container, tube, or kit is for human use or human treatment, for example human wound treatment. In one embodiment, the container, tube, or kit may be used for animals, or adapted for veterinary use or animal treatment, for animal wound treatment.

In another aspect, the present invention provides use of a container or tube as herein described for the preparation of a topical gel or topical membrane or topical patch.

In another aspect, the present invention provides a topical gel or topical membrane or topical patch obtained from a container or tube as herein described or a method as herein described.

Preferably, the containers according to any of the aspects of the invention are steam sterilized, preferably at about 121° C., or >than 100° C., or >than 110° C., or >than 115° C., or >than 120° C. Other sterilization procedures may affect the integrity, the structure of the various substances contained in the containers.

Embodiments of the present invention will now be described in more detail with reference to the accompanying Figures and Example:

Example 1: Preparation of a 2% Hyaluronic Acid Gel with PPI Water and Calcium Gluconate In order to use a PRP or BMC-coagulation activator combination in wound healing, it is necessary to obtain a gel or membrane or patch structure for topical application into the wounds.

To provide a gel structure for topical application, the manufacturing process for hyaluronic acid was modified. The diluting agent PBS was replaced with water for injections (PPI). It has been found that the viscosity of hyaluronic acid within the PRP or BMC-coagulation activator combination of the present invention has been maintained despite the presence of the coagulation activator. This surprising reduction in viscosity (in the presence of the coagulation activator) has been achieved due to replacing PBS with PPI water during the preparation of hyaluronic acid.

In order to prepare the 2% hyaluronic acid gel with PPI water and calcium gluconate, the first stage is to prepare a PPI Water (BBraun) and Calcium Gluconate CaGlu solution.

The amount of hyaluronic acid to be added to this solution to provide a 2% hyaluronic gel is calculated as follows:

Hyaluronic acid weighing calculation: 1550 Kda/PHI 3978:575*2/100=11.5 g

Calculation allowing for loss on drying (13.2%): 11.5/0.868=13.24 g 13.24 g of hyaluronic acid fibers are introduced into the kenwood mixer containing the PPI water and calcium gluconate.

The mixture is mixed together for 3 hours and 30 minutes at a low speed (speed 1) to provide a homogeneous, viscous, transparent shiny gel comprising 2% hyaluronic acid and calcium gluconate (HA-CaGlu).

The amount of hyaluronic acid to be added to a solution to provide a

Example 2: Preparation of Platelet-Rich Plasma-Hyaluronic Acid-Calcium Gluconate Tubes Each tube (125 mm) is filled with 2 g of the hyaluronic acid-calcium gluconate (HA-Caglu) gel prepared in Example 1, 3 g of thixotropic gel and 0.6 ml of sodium citrate with 6 ml of vacuum.

0.3 ml of calcium gluconate for 40 mg hyaluronic acid (HA) was introduced into each tube.

Twenty tubes were prepared in this manner.

The tubes were steam sterilized at 121° C.

Example 3-Formation of Topical Gel or Topical Patch or Topical Membrane

The tubes of Example 2 were used to prepare a topical gel or topical patch or topical membrane from Platelet Rich Plasma obtained from five donors (Donor 1, Donor 2, Donor 3, Donor 4, Donor 5) and the results are shown in FIGS. 1*a-f*, FIGS. 2*a-f* and FIGS. 3*a-f*.

In vitro tests were carried out to certify the conditions of preparation of the product in gelled form after deposition in a petri dish.

The resultant products were qualified according to a visual check to determine whether a gelled structure was formed or not after waiting for a period of 10 minutes at room temperature.

Materials Used:

Centrifuge RegenLab Drucker;

Tubes of Example 2;

5 blood donors, 36 mL of blood/patient is collected from each donor (an additional sample is collected from Donor 3 and tested to assess pH and osmolarity (see Example 5 4));

0.3 mL of calcium gluconate per tube;

9 petri dishes 60×15 mm Becton Dickinson, Caglu 5 ml.

Total blood volume needed: 60 mL

Figure 1B:
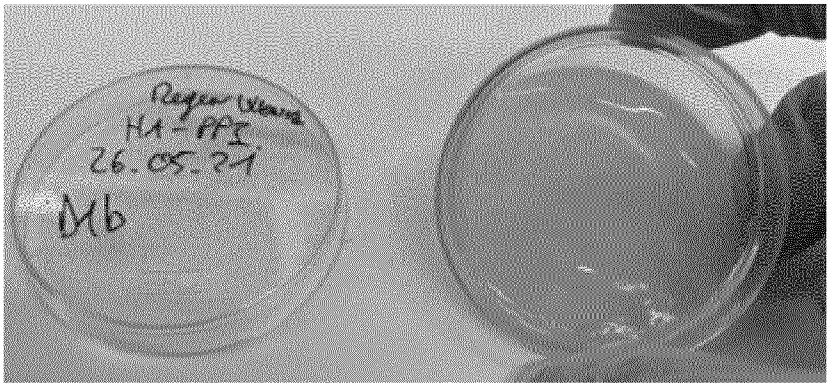
Figure 1C:
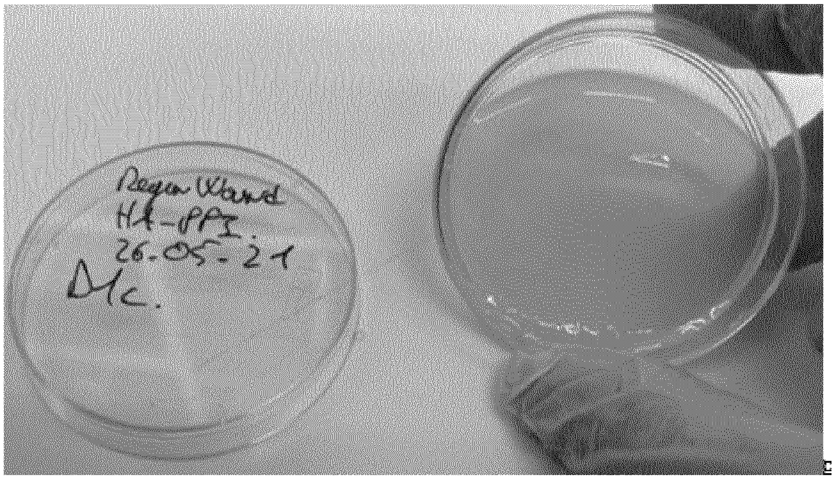

Donor 1:3 ml of Platelet rich plasma and 2 ml of hyaluronic acid-calcium gluconate combination (HA-Ca-Glu) within the tube. The tube therefore contains 10% of calcium gluconate compared to the volume of platelet rich plasma. After 10 minutes, it can be seen for the three samples from Donor 1 that a semi-solid membrane has formed which does not flow (FIGS. 1*a*-*c*).

Donor 2:3 ml of Platelet rich plasma and 2 ml of hyaluronic acid-calcium gluconate combination (HA-Ca-Glu) within the tube. The tube therefore contains 10% of calcium gluconate compared to the volume of platelet rich plasma.

Figure 2A:
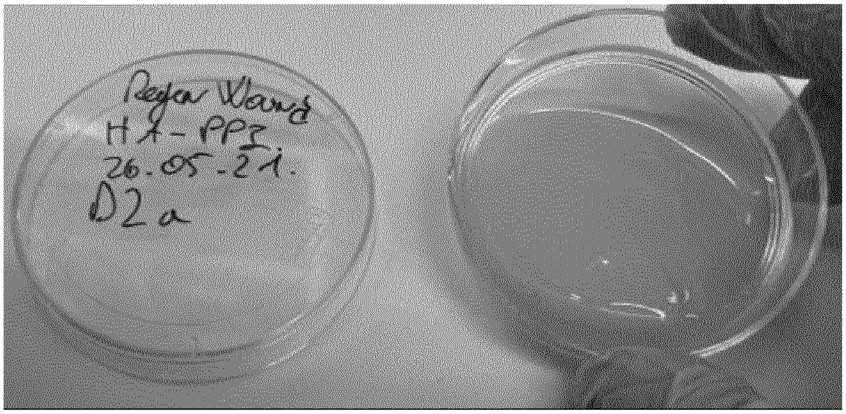
FIGS. 2*a* to 2*c* are photographs illustrating topical gels for topical application onto or into wounds obtained using Platelet-Rich Plasma obtained from Donor 2 and a container and method according to embodiments of the present invention.
Figure 2B:
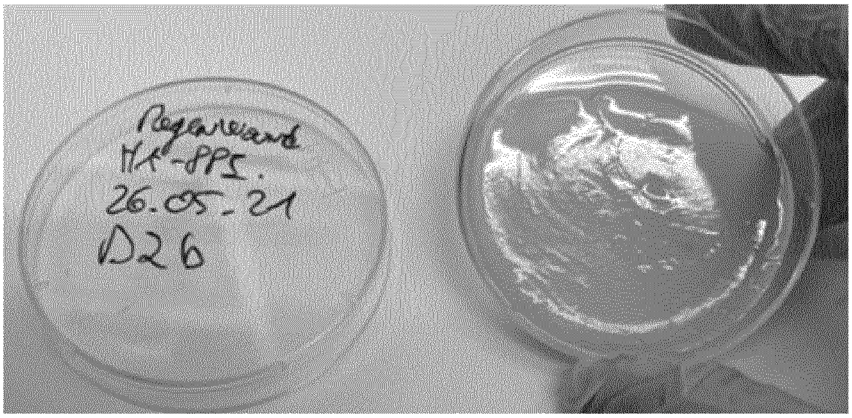
Figure 2C:
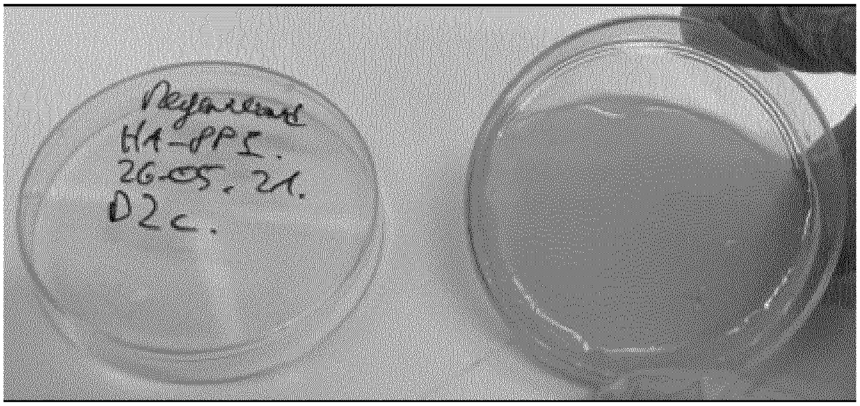

After 10 minutes, it can be seen for the three samples from Donor 2 that a semi-solid membrane has formed which does not flow (FIGS. 2*a*-*c*).

Donor 3:3 ml of Platelet rich plasma and 2 ml of hyaluronic acid-calcium gluconate combination (HA-Ca-Glu) within the tube. The tube therefore contains 10% of calcium gluconate compared to the volume of platelet rich plasma.

Figure 3A:
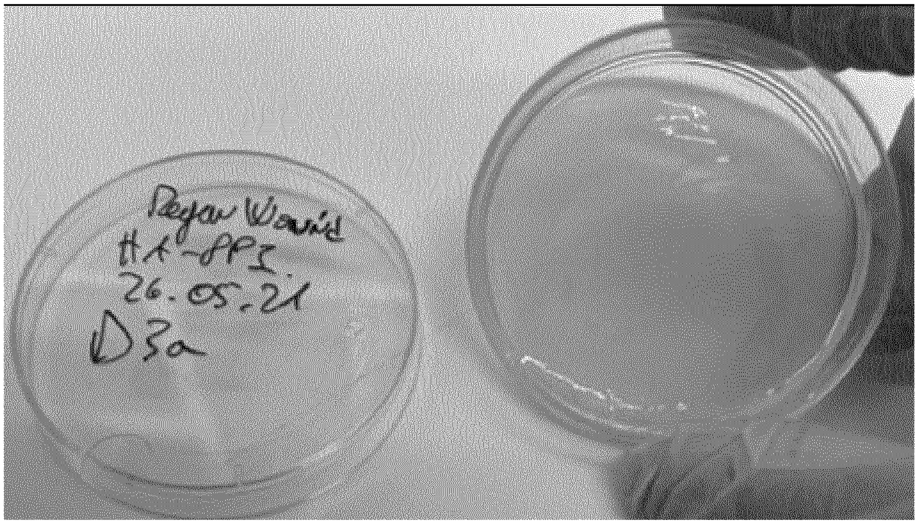
FIGS. 3*a* to 3*c* are photographs illustrating topical gels for topical application onto or into wounds obtained using Platelet-Rich Plasma obtained from Donor 3 and a container and method according to embodiments of the present invention.
Figure 3B:
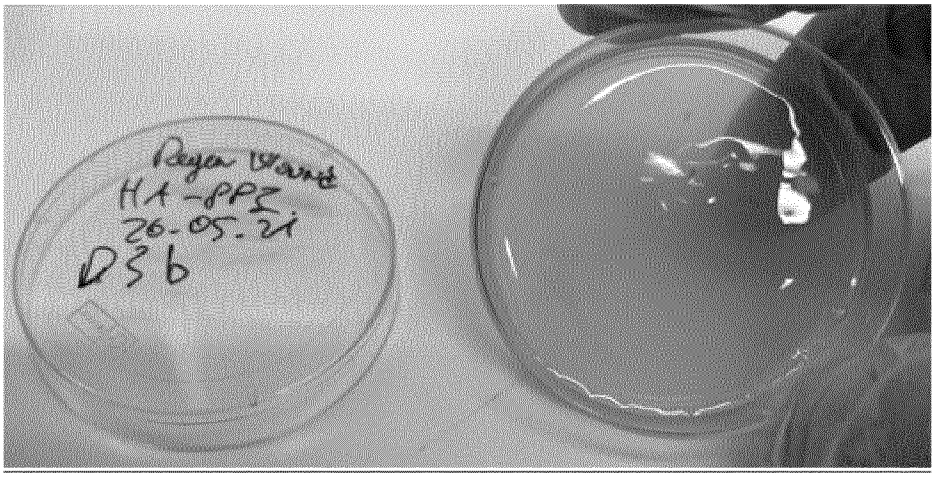
Figure 3C:
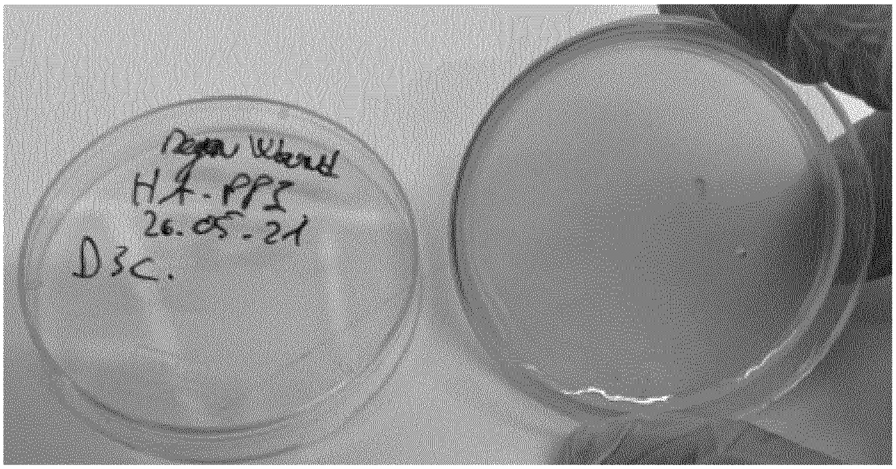

After 10 minutes, it can be seen for the three samples from Donor 3 that a semi-solid membrane has formed which does not flow (FIGS. 3*a*-*c*).

The nine samples were found to be consistent in providing a gel or membrane or patch which does not flow and would be suitable for topical use in the treatment of wounds.

Example 4: PH and Osmolarity Assessment

Figure 4:
FIG. 4 is a photograph of the results of a pH assessment of an isolated plasma-derived product obtained from Donor 3 using the container and method of the present invention.
Figure 5:
FIG. 5 is a photograph of the results of an osmolarity assessment of an isolated plasma-derived product obtained from Donor 3 using the container and method of the present invention.
Figure 6A:
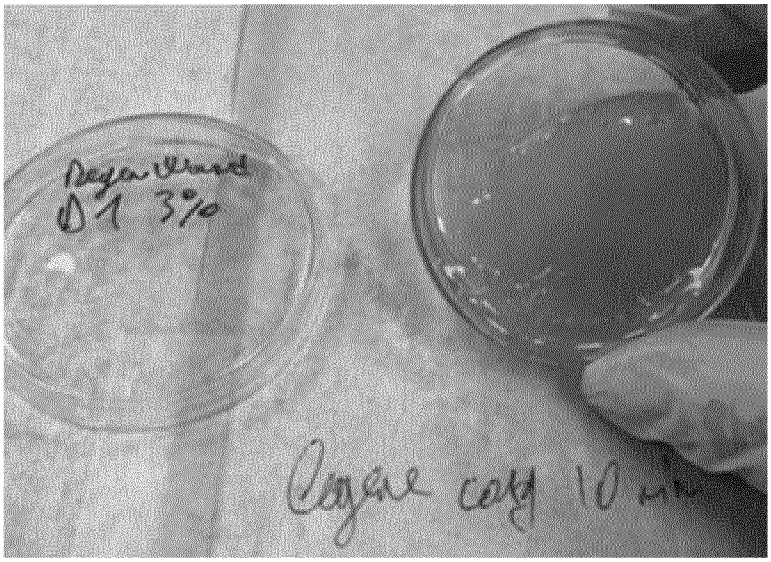
FIGS. 6*a* to 6*f* are photographs illustrating topical gels formed using PRP-coagulation activator combinations using six different solutions of coagulation activator comprising varying concentrations of coagulation activator and PRP from Donor 1.
Figure 6B:
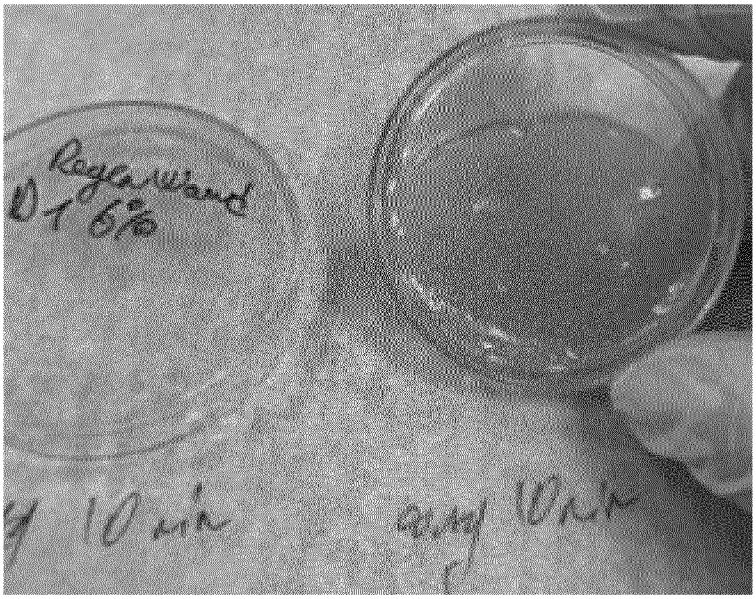
Figure 6C:
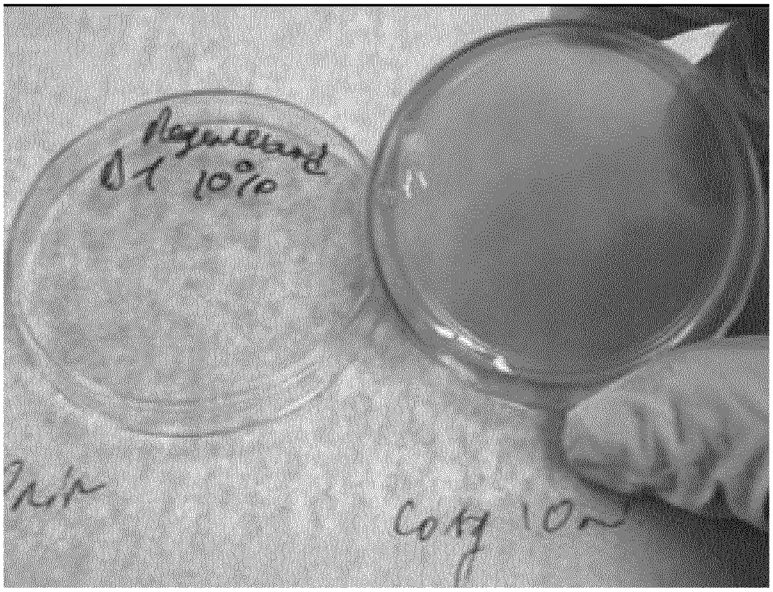
Figure 6D:
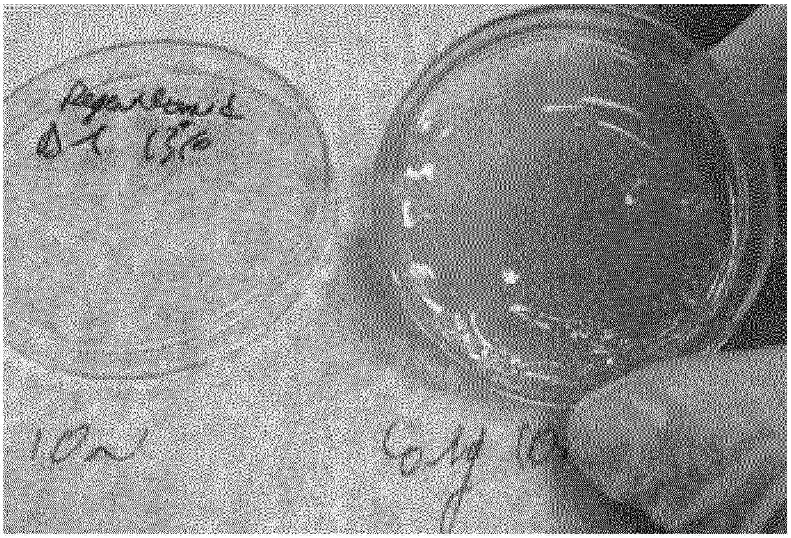
Figure 6E:
Figure 6F:
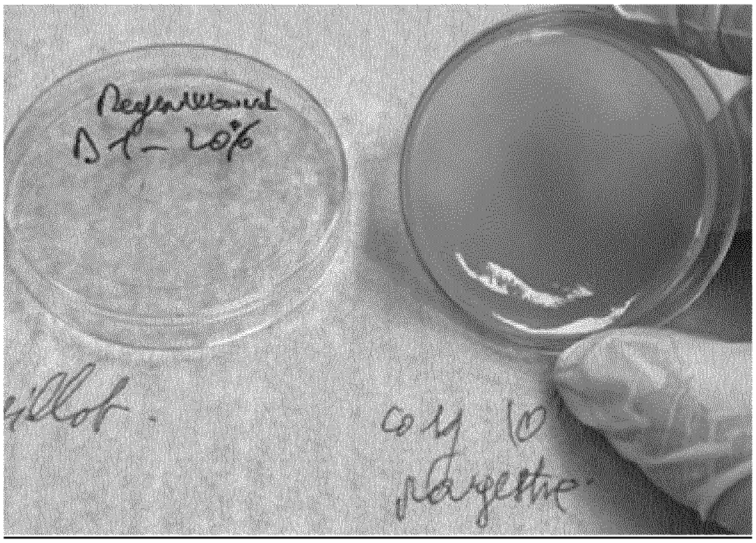

A sample from Donor 3 was assessed to determine pH and Osmolarity of the obtained platelet rich plasma-hyaluronic acid and calcium gluconate mixture from the tubes of Example 2. The results are shown in FIGS. 4 and 5.

It can be seen that the mixture was found to have a pH of 7.43 and an osmolarity of 302 mOsm which is within the desired range of 280-330 mOsm.

Example 5-Investigation of Range of Action of Coagulation Activator

In order to determine the range of action of calcium gluconate added to the hyaluronic acid (HA) preparation, several solutions were prepared with different quantities of calcium gluconate in order to provide tubes containing different rations of calcium gluconate to PRP.

The details of the contents of each composition comprising coagulation activator, in this case calcium gluconate are detailed below.

PRP was obtained from each of six donors.

In vitro tests were carried out to certify the conditions of preparation of the product in gelled form after deposition in a petri dish.

Photographs of the results are shown in FIGS. 6*a* to 6*e* for the gelled products obtained using PRP from donor 1. Highly similar results were obtained in relation to PRP obtained from each of the six donors.

The resultant products were qualified according to a visual check to determine whether a gelled structure was formed or not after waiting for a period of 10 minutes at room temperature.

Method for Preparation of Calcium Gluconate Solution:

The coagulation activator, calcium gluconate, used for all of the tubes was prepared as follows:

9 g of Calcium Gluconate monohydrate was weighed in a 100 ml volumetric flask.

The flask was adjusted to obtain a 100 ml solution of calcium gluconate in PPI water. The solution was heated at 80° C. on a magnetic hot plate for 1 hour and stirred at agitation speed 1 to create a vortex. A white to transparent solution was produced. The solution was subsequently filtered using a 0.22 μm filter to remove any particles.

Calcium Gluconate Solutions:

Six solutions were prepared, each solution containing a different concentration of coagulation activator, calcium gluconate. These solutions were as follows:

Solution 1: 3% of CaGlu relative to the quantity of PRP obtained (3 mL)

Preparation of 50 ml PPI+2.5 ml Caglu10%

Weighing of HA HTL 4043A (52.5*2/100=1.05 g), with Loss On Drying (LOD) (1.05/0.862=1.21 g)

Solution 2: 6% of CaGlu relative to the quantity of PRP obtained (3 mL)

Preparation of 50 ml PPI+5 ml Caglu10%

Weighing of HA HTL 4043A (55*2/100=1.1 g), with LOD (1.1/O.862=1.27 g)

Solution 3: 10% of CaGlu relative to the quantity of PRP obtained (3 mL)

Preparation of 50 ml PPI+7.5 ml Caglu 10%

Weighing of HA HTL 4043A (57*2/100=1.15 g), with LOD (1.15/0.862=1.33 g)

Solution 4: 13% of CaGlu relative to the quantity of PRP obtained (3 mL)

Preparation of 50 ml PPI+10 ml Caglu 10%

Weighing of HA HTL 4043A (60*2/100=1.2 g), with LOD (1.20/0.862=1.39 g)

Solution 5: 16% of CaGlu relative to the quantity of PRP obtained (3 mL)

Préparation 50 ml PPI+12.5 ml Caglu 10%

Weighing of HA HTL 4043A (62.5*2/100=1.25 g), with LOD (1.25/0.862=1.45 g)

Solution 6: 20% of CaGlu relative to the quantity of PRP obtained (3 mL)

Preparation of 50 ml PPI+15 ml Caglu 10%

Weighing of HA HTL 4043A (65*2/100=1.3 g), with LOD (1.3/0.862=1.50 g)

Each solution, containing water for injection (PPI), calcium gluconate (Caglu) and hyaluronic acid (HA), was introduced into a Kenwood mixer.

The solutions were mixed for 3 hours 30 minutes at a speed setting of 1.

Materials Used:

- Centrifuge RegenLab Drucker;
- Medical devices: RegenWound (PRP-HA-CaGlu)
- 6 different solutions comprising differing concentrations of CaGlu (as above);
- 5 blood donors, 6 tubes collected from each donor (36 mL of blood/patient is collected)
- 0.3 mL of calcium gluconate per tube;
- 30 petri dishes 60×15 mm Becton Dickinson, Caglu 5 ml.
- Total blood volume needed: 180 mL Results For each test carried out, gelling of the PRP-coagulation activator combination was observed a few minutes after having homogenized the mixture after centrifugation. Each solution produced a homogeneous, viscous, transparent, shiny gel. The results of the PRP-coagulation activator combination obtained using each of the above solutions using PRP obtained from each of the five donors is shown below in Table 1.

TABLE 1

| | Donor 1 | Donor 2 | Donor 3 | Donor 4 | Donor 5 |
|---|---|---|---|---|---|
| Solution 1 3% CaGlu | Slightly coagulated | Slightly coagulated, liquid | Coagulated, homogenous | Liquid | Coagulated, homogenous |
| Solution 2 6% CaGlu | Coagulated, non-homogenous | Coagulated, non-homogenous | Coagulated, homogenous | Coagulated, homogenous | Coagulated, homogenous |
| Solution 3 10% CaGlu | Coagulated, homogenous | Coagulated, homogenous | Coagulated, homogenous | Coagulated, homogenous | Coagulated, homogenous |
| Solution 4 13% CaGlu | Coagulated, non-homogenous | Coagulated, homogenous | Coagulated, homogenous | Coagulated, homogenous | Coagulated, homogenous |
| Solution 5 16% CaGlu | Clot and liquid | Clot with part of the gel and liquid | Clot and liquid | Coagulated, homogenous | Clot with part of the gel, liquid |
| Solution 6 20% CaGlu | Coagulated, reddish | Coagulated, reddish | Coagulated, reddish | Coagulated, reddish | Clot with part of the gel, liquid |

The results shown that a coagulated, homogeneous substance, for example a gel, membrane or patch, is provided after ten minutes by a PRP-coagulation activator combination (comprising calcium gluconate as the coagulation activator) obtained using a solution comprising at least 6% calcium gluconate. A coagulated, homogenous substance for example a gel, membrane or patch, is provided after ten minutes by a PRP-coagulation activator combination (comprising calcium gluconate as the coagulation activator) obtained using a solution comprising preferably up to 16%, preferably up to about 20% calcium gluconate.

Results show that a percentage>20% of CaGlu relative to the quantity of PRP obtained (3 mL) or a percentage<3% of CaGlu relative to the quantity of PRP obtained (3 mL) do not produce stable products.

It is to be noted that although the Example relates to PRP-coagulation activator combinations, that similar results are obtained with BMC-coagulation activator combinations.

It is also the be noted that although the Example relates to PRP-calcium gluconate combinations, that similar results are obtained with other suitable coagulation activators.

By adding coagulation activator, preferably calcium gluconate, and by replacing PBS in the hyaluronic acid preparation step with PPI water, the viscosity of the mixture is slightly reduced thereby allowing improved homogenization after centrifugation.

Example 6-pH Assessment

The pH values of the PRP-coagulation activator combinations obtained from the use of each of the six solutions on PRP obtained from each donor were assessed. The results are shown in Table 2:

TABLE 2

| | pH Values | | | | | |
|---|---|---|---|---|---|---|
| | Solution 1 3% Coagulation Activator | Solution 2 6% Coagulation Activator | Solution 3 10% Coagulation Activator | Solution 4 13% Coagulation Activator | Solution 5 16% Coagulation Activator | Solution 6 20% Coagulation Activator |
| Donor 1 | 8.15 | 8.03 | 8.46 | 8.16 | 8.19 | 8.16 |
| Donor 2 | 8.26 | 8.05 | 7.94 | 8.07 | 7.80 | 8.02 |
| Donor 3 | 8.01 | 8.04 | 8.07 | 7.94 | 8.02 | 7.98 |
| Donor 4 | 7.93 | 7.89 | 7.87 | 7.78 | 7.72 | 7.73 |
| Donor 5 | 7.79 | 7.72 | 7.69 | 7.73 | 7.67 | 7.48 |
| Mean | 8.028 | 7.946 | 8.006 | 7.936 | 7.88 | 7.874 |
| Std Dev | 0.18390215 | 0.1422322 | 0.2884961 | 0.18365729 | 0.21897488 | 0.26940676 |

It can be seen that the average pH of the PRP-coagulation activator combinations obtained using each of the solutions above with PRP obtained from the five donors is within the range of 7.5 to 8.5, preferably within the range of 7.7 to 8.2, preferably within the range of 7.9 to 8.

This pH of the combinations is acceptable for use in wound healing treatments.

It is to be noted that although the Example relates to PRP-coagulation activator combinations, that similar results are obtained with BMC-coagulation activator combinations.

It is also the be noted that although the Example relates to PRP-calcium gluconate combinations, that similar results are obtained with other suitable coagulation activators.

Example 7-Osmolarity Assessment

The Osmolarity values of the PRP-coagulation activator combinations obtained from the use of each of the six solutions on PRP obtained from each donor were assessed. The results are shown in Table 3:

TABLE 3

| | Osmolarity Values (mOsm) | | | | | |
|---|---|---|---|---|---|---|
| | Solution 1 3% Coagulation Activator | Solution 2 6% Coagulation Activator | Solution 3 10% Coagulation Activator | Solution 4 13% Coagulation Activator | Solution 5 16% Coagulation Activator | Solution 6 20% Coagulation Activator |
| Donor 1 | 209 | 149 | 147 | 145 | 153 | 146 |
| Donor 2 | 147 | 152 | 148 | 150 | 152 | 148 |
| Donor 3 | 196 | 162 | 151 | 148 | 145 | 147 |
| Donor 4 | 188 | 165 | 153 | 150 | 146 | 149 |
| Donor 5 | 201 | 173 | 147 | 149 | 152 | 156 |
| Mean | 188.2 | 160.2 | 149.2 | 148.4 | 149.6 | 149.2 |
| StdDev | 24.2631408 | 9.78263768 | 2.68328157 | 2.07364414 | 3.78153408 | 3.96232255 |

It can be seen that the average osmolarity values for the PRP-coagulation activator combinations obtained using the six solutions above using PRP obtained from the five donors is within the range of from 140 to 220, preferably from 150 to 200, preferably from 150 to 190.

The osmolarity of the combination is suitable for use in wound healing treatments.

It is to be noted that although the Example relates to PRP-coagulation activator combinations, that similar results are obtained with BMC-coagulation activator combinations.

It is also the be noted that although the Example relates to PRP-calcium gluconate combinations, that similar results are obtained with other suitable coagulation activators.

It has been found that the viscosity of hyaluronic acid within the PRP or BMC-coagulation activator combination of the present invention has been maintained despite the presence of the coagulation activator. This surprising reduction in viscosity (in the presence of the coagulation activator) has been achieved due to replacing PBS with PPI water during the preparation of hyaluronic acid.

The PRP or BMC-coagulation activator combinations of the present invention combine the beneficial effects of PRP or BMC and hyaluronic acid whilst providing a topical gel or membrane or patch for the treatment of chronic wounds. Similar results may be obtained with other suitable biomaterials.

Example 8-Thixotropic Gel

An example of a thixotropic gel according to one embodiment of the present invention is provided in Table 4:

TABLE 4

| Component | Concentration (%) |
|---|---|
| Trioctyl trimellitate | 52.26 |
| Dimethyl dichlorosilane | 7.99 |
| cycloaliphatic hydrocarbon resin | 39.65 |
| tris (2,4-di-tert-butylphenyl) phosphite | 0.05 |
| tetrakis (3-(3,5-di-tert-butyl-4-hydroxyphenyl) propionate of pentaerythritol) | 0.05 |

Example 9-Platelet Recovery Per Ml of Extracted Blood

The container of the present invention comprising thixotropic gel and sodium citrate was used in comparison to conventional devices to determine the platelet recovery per ml of extract blood for each container. The results are shown in Table 5 and in FIG. 7.

TABLE 5

| | Container of Present Invention (RegenGelT) | Arthrex ACP | BTI PRGF/endoret | Biomet GPSIII | Harvest SmartPrep2 | Arthrex Angel | Arteriocyte Magellan | Emcyte |
|---|---|---|---|---|---|---|---|---|
| PLT X Factor | 1.4 | 1.6-2 | 2-3 | | | | | 6.7 |
| Recovery rate (%) | 77 | 60 | 50 | 43 | 65 | 40 | 21 | 70 |
| Vol Blood extracted (ml) | 10 | 15 | 8 | 27 | 27 | 35 | 26 | 60 |
| Vol PRP (ml) | 5.5 | 5 | 1.5 | 3 | 3 | 3 | 3 | 7 |
| Standard platelet count in the blood (mm$^3$ sang) | 200000 | 200000 | 200000 | 200000 | 200000 | 200000 | 200000 | 200000 |
| Platelet count in the blood extracted | 2000000 | 3000000 | 1600000 | 5400000 | 5400000 | 7000000 | 5200000 | 12000000 |
| Platelet count in PRP in function of recovery rate | 1540000 | 1800000 | 800000 | 2322000 | 3510000 | 2800000 | 1092000 | 8400000 |
| Platelet count per ml of blood extracted | 154000 | 120000 | 100000 | 86000 | 130000 | 80000 | 42000 | 140000 |

Figure 7:
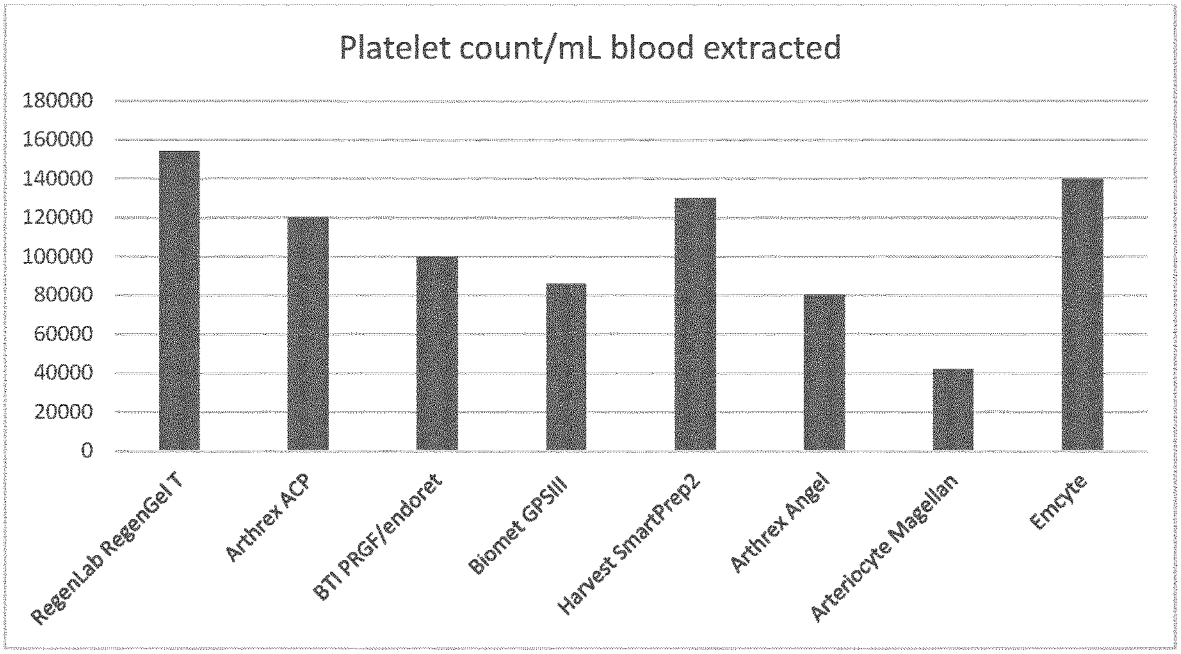
FIG. 7 is a graph illustrating the platelet count per ml of blood extracted using a container of the present invention in comparison to conventional devices.

It can be seen from Table 5 and FIG. 7 that the container of the present invention provides for an improved platelet count per ml of blood extracted compared to conventional devices. In particular, it can be seen that the container of the present invention provided at least a 10% increase in platelet count (per ml of extract blood) compared to that achieved using a conventional device (Emcyte).

Example 10-Adherence Properties

Figure 8:
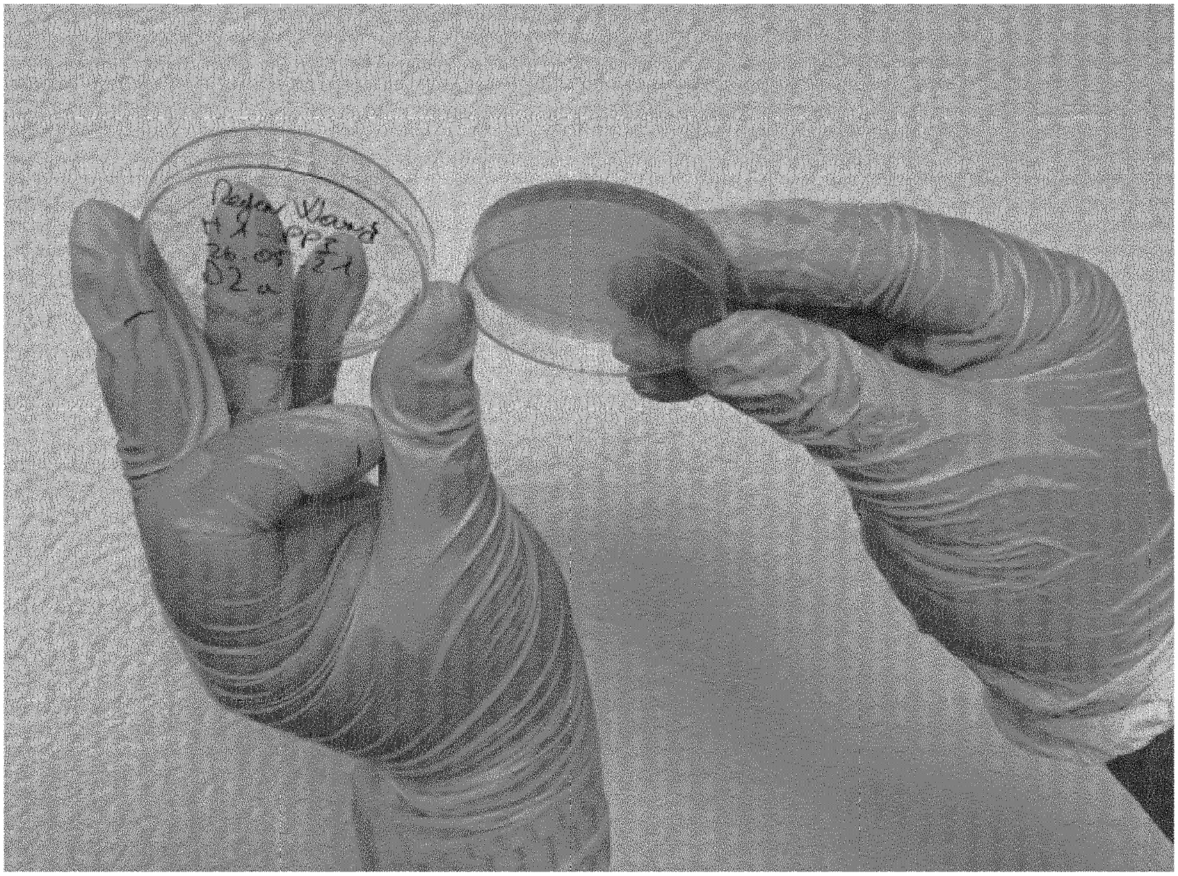
FIG. 8 is a photo illustrating the adherence of a topical gel, membrane or plasma formed using the PRP-coagulation activator combinations using a container according to one embodiment of the present invention.

FIG. 8 illustrates the adherence properties of a topical gel, membrane or patch formed using a container of the present invention. It can be seen that the topical gel, membrane or patch formed remains adhered to the plastic petri dish when inverted. The present invention can therefore be used to provide membranes with improved adherence for wounds and as such will remain in place providing improved protection. In contrast, conventional membranes remain fluid and have poor adherence properties providing ineffective wound membranes.

The invention claimed is:

1. A container for use in the preparation of a topical gel or topical membrane or topical patch formed from at least one biomaterial and a platelet-rich plasma (PRP) and/or bone marrow concentrate (BMC)-coagulation activator combination, in which the container is prefilled with or comprises an anticoagulant, at least one thixotropic gel, and a composition comprising at least one coagulation activator and at least one biomaterial; wherein said composition comprising at least one coagulation activator and at least one biomaterial is located beneath the at least one thixotropic gel, or at a more distal end of the container than the at least one thixotropic gel; and wherein said anticoagulant is located above the at least one thixotropic gel, or at a more proximal end of the container than the at least one thixotropic gel.

2. The container according to claim 1, wherein said at least one thixotropic gel is characterized by a density selected from about 1.04 g/cm$^3$ to about 1.095 g/cm$^3$.

3. The container according to claim 2, wherein said at least one thixotropic gel comprises trioctyl trimellitate, silica, hydrocarbon resin, phenol(s) and phosphite ester.

4. The container as claimed in claim 2, in which the at least one thixotropic gel comprises trioctyl trimellitate in the range of about 40 to about 60% by weight, silica in the range of about 2 to about 10% by weight, hydrocarbon resin in the range of about 30 to about 60% by weight; phenol(s) in the range of about 0 to about 1% by weight, and phosphite ester in the range of about 0% to about 0.06% by weight, wherein said at least one coagulation activator is calcium gluconate.

5. The container as claimed in claim 4, in which the at least one coagulation activator is present within the container in an amount of up to about 20% v/v relative to the amount of PRP or BMC.

6. The container according to claim 1, in which the at least one biomaterial, in which the biomaterial is hyaluronic acid, and in which the hyaluronic acid and the at least one coagulation activator are PBS free.

7. The container according to claim 6, wherein said anticoagulant is sodium citrate.

8. A container for use in the preparation of a topical gel or topical membrane or topical patch formed from at least one biomaterial and a Platelet-rich Plasma (PRP) and/or bone marrow concentrate (BMC)-coagulation activator combination, in which the container is prefilled with or comprises an anticoagulant, a thixotropic gel, and a composition comprising at least one coagulation activator and at least one biomaterial, wherein said composition comprising at least one coagulation activator and at least one biomaterial is located beneath the thixotropic gel, or at a more distal end of the container than the thixotropic gel, and wherein said anticoagulant is located above the thixotropic gel, or at a more proximal end of the container than the thixotropic gel.

9. The container according to claim 8, wherein the composition comprising the at least one coagulation activator and the at least one biomaterial form a single layer or composition.

10. A container for use in the preparation of a topical gel or topical membrane or topical patch formed from a hyaluronic acid, and a platelet-rich plasma (PRP) and/or bone marrow concentrate (BMC)-coagulation activator combination, in which the container is prefilled with or comprises:

a) an anticoagulant;

b) a thixotropic gel characterized by a density selected from about 1.04 g/cm$^3$ to about 1.95 g/cm$^3$; and a composition comprising:

c) hyaluronic acid, and d) a coagulation activator, wherein said thixotropic gel is provided as a layer positioned above the composition comprising hyaluronic acid and coagulation activator from the distal end of said container, in which the composition comprising hyaluronic acid and coagulation activator are provided either as separate layers or mixed together within a single layer or composition, and in which the anticoagulant is provided as a further layer positioned above the layer of thixotropic gel from the distal end of said container.

11. The container according to claim 10, wherein said coagulation activator is calcium gluconate, and wherein said thixotropic gel is selected from: an oligomer, polymer, polyolefin hydrocarbon oligomer, polyester gel, an acrylic resin mixture, a polyethylene glycol (PEG)-silica gel, a polyoxyalkylene polyol, trioctyl trimellitate, a hydrocarbonated resin, silica dimethyl silylate, or any combination thereof.

12. The container as claimed in claim 10, in which the container is a centrifugation tube closed to the atmosphere.

13. The container as claimed in claim 10, prefilled with one or more of: thrombin serum, tricalcium phosphate (TCP), a bone substitute, hyaluronic acid composition, calcium gluconate, calcium saccharate, chitosan, fibroin, fibroin-silk protein or fibroin proteins, growth factors, mannitol, collagen, albumin, ascorbic acid, cream, fat cells, fat tissue, bone marrow concentrate, lubricin, cd-gelatin, botulinum toxin and/or one or more autologous cell extracts selected from an extract of keratinocytes, bone marrow, fibroblasts, periosteum or corneal cells, melanocytes and Langerhans cell, fat cells, muscle cells, myoblasts, satellite cells, osteoblasts, chondrocytes, umbilical cord cells, stem cells, mesenchymal stem cells (MSCs), preadipocytes, preendothelial cells, Schwann cells or Achilles tendon cells, or any combination thereof.

14. The container as claimed in claim 10, wherein the container creates an isolated plasma-derived product or bone marrow-derived product.

15. The container as claimed in claim 10, wherein the container creates an isolated plasma-derived product or bone marrow-derived product for use as drug or a medicament, or for use in wound healing or for use as a topical gel, topical membrane or topical patch.

16. The container as claimed in claim 10, wherein the container creates an isolated plasma derived product or bone marrow derived product having an osmolarity in the range of between about 280 to about 330 mOsm/l.

17. The container as claimed in claim 10, wherein the container creates an isolated plasma derived product or bone marrow derived product in which the container was prefilled or comprises between about 3% to about 20% v/v coagulation activator relative to the quantity of PRP or BMC.

18. The container as claimed in claim 10, wherein the container creates an isolated plasma derived product or bone marrow derived product in which the pH of the product is in the range of from about 7.5 to about 8.5.

19. The container as claimed in claim 10, wherein the container creates an isolated plasma derived product or bone marrow derived product in which the osmolarity is in the range of from about 140 to about 220 mOsm/l.

* * * * *